US007767770B2

(12) United States Patent
Han et al.

(10) Patent No.: US 7,767,770 B2
(45) Date of Patent: Aug. 3, 2010

(54) PROCESS FOR THE OXIDATIVE DEHYDROGENATION OF ETHANE

(75) Inventors: Scott Han, Lawrenceville, NJ (US); Daniel J. Martenak, Perkasie, PA (US); Lei Jin, Vernon, CT (US); Steven Lawrence Suib, Storrs, CT (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/586,146

(22) Filed: Sep. 17, 2009

(65) Prior Publication Data

US 2010/0087615 A1    Apr. 8, 2010

Related U.S. Application Data

(60) Provisional application No. 61/192,395, filed on Sep. 18, 2008.

(51) Int. Cl.
  *C08F 2/00*   (2006.01)
  *C07C 5/333*  (2006.01)
  *B01J 23/24*  (2006.01)

(52) U.S. Cl. .................. 526/75; 423/418.2; 528/392; 560/233; 568/451; 568/461; 585/330; 585/638; 585/654

(58) Field of Classification Search ............. 585/330, 585/638, 654; 526/75; 528/392; 560/233; 568/451, 461; 423/418.2
See application file for complete search history.

(56) References Cited

U.S. PATENT DOCUMENTS

| 3,530,109 | A   |   | 9/1970  | Fenton        |         |
|-----------|-----|---|---------|---------------|---------|
| 3,694,412 | A   |   | 9/1972  | Nozaki        |         |
| 4,408,079 | A   |   | 10/1983 | Merger et al. |         |
| 5,597,944 | A   | * | 1/1997  | O'Young et al.| 585/654 |
| 6,284,919 | B1  |   | 9/2001  | Pearson et al.|         |
| 7,700,517 | B2  | * | 4/2010  | Li et al.     | 502/324 |

FOREIGN PATENT DOCUMENTS

EP    0710623  A1    5/1996

OTHER PUBLICATIONS

Frock, S.I.,et al. "A Review of Porous Manganese Oxide Materials" Chem. Matter, vol. 10. No. 10. 1998, p. 2619-2628, University of Connecticut, Dept. of Chem., Storr, CT.
Mimura, N., et al."High-Performance Cr/H-ZSM-5 Catalysts for Oxidative Dehydrogentation Ethane to Ethylene with CO2 as an Oxidant" Catalyst Communication 3(2002) 257-262, AIST.
Li, Y.N., et al. "Estimation of Consecutive and Parallel Reactions During Ethane Dehydrogenation with Carbon Dioxide Over Co-MCM-41" Polish J. Chem., 79, 1357-1364 (2005).

* cited by examiner

*Primary Examiner*—Fred M Teskin
(74) *Attorney, Agent, or Firm*—Tifani M. Cottingham

(57) ABSTRACT

A method for producing a mixture of ethylene and carbon monoxide by contacting ethane and an oxygen source with a catalyst comprising synthetic cryptomelane or octahedral molecular sieve. The method further comprises condensing the alkyl propionate with formaldehyde to produce an alkyl methacrylate.

10 Claims, No Drawings

PROCESS FOR THE OXIDATIVE DEHYDROGENATION OF ETHANE

This application claims the benefit of priority under 35 U.S.C. §119(e) of U.S. Provisional Patent Application No. 61/192,395 filed on Sep. 18, 2008.

The present invention relates to an improved catalytic process for producing ethylene and carbon monoxide mixtures from ethane and carbon dioxide, and further to various integrated processes for producing alkyl propionates or methacrylic acid esters from ethane and carbon dioxide.

Ethylene and carbon monoxide mixtures are used as a feedstock for homologation of ethylene to propionic acid derivatives. For example, carbonylation of ethylene to produce methyl propionate, followed by condensation with formaldehyde, is an important commercial route to methyl methacrylate. For example, U.S. Pat. No. 6,284,919 discloses a process for carbonylation of ethylene to methyl propionate. In the first step of this process, ethylene, CO, and methanol feed is converted to methyl propionate. The ethylene and CO feeds used would generally be from conventional sources such as steam cracking and methane steam reforming. However, due to the high cost associated with these ethylene-producing processes, because ethylene is a relatively expensive starting material, more economic alternatives are needed. A process that uses ethane, which is a component of natural gas, as a starting material would be economically desirable due to the large price difference between ethane and ethylene. An integrated process which provides for the production of esters such as methyl propionate and methyl methacrylate using cheap and abundantly available feeds would be of high value. In addition, ethylene and carbon monoxide feeds often are combined with hydrogen in the industrially important hydroformylation reaction. This reaction, also known as the oxo reaction, is used mainly for conversion of olefins to aldehydes and alcohols.

The problem addressed by this invention is to provide an alternative catalytic process for producing mixtures of ethylene and carbon monoxide suitable as a feedstock for other processes.

The present invention provides a method for producing a mixture of ethylene and carbon monoxide by contacting ethane and carbon dioxide with a catalyst comprising synthetic cryptomelane or octahedral molecular sieve at a temperature of at least 550° C. to produce ethylene and carbon monoxide.

Percentages are weight percentages, and temperatures are in ° C., unless specified otherwise. An alkyl group is a saturated hydrocarbyl group having from one to twenty carbon atoms, and may be linear or branched. Preferably, alkyl groups have from one to eight carbon atoms, alternatively from one to four carbon atoms, alternatively one or two carbon atoms, alternatively one carbon atom. The alcohol used in the ethylene carbonylation reaction corresponds to an alkyl group, as defined above, substituted with a hydroxyl group.

In some embodiments of the invention, the catalyst used in the reaction of ethane and carbon dioxide is a synthetic cryptomelane octahedral molecular sieve (OMS) material. The catalyst structure comprises a 2×2 tunnel structure material made of 2 octahedral $MnO_6$ units that are shared by edges and vertices. These materials are mixed valent which leads to a charge imbalance which is made up by having cations in the tunnel sites. In the case of the OMS-2 catalyst of the present invention, useful cations include but are not limited to Na, Li, Rb, Cs and K. The mixed valency of manganese leads to a semi-conducting material. In the catalytic reactions of the present invention the catalyst is further modified with a transition element to enhance activity and selectivity. As used herein by "modified with a transition element" means the addition of at least one transition element or an oxide of at least one transition element to the support using techniques well-known to those skilled in the art including but not limited to incipient wetness, co-precipitation, vapor deposition, and ion-exchange. Transition elements useful in the present invention include but are not limited to Fe, Co, Ni, Mn, Cr, V, Ti, Cu, and Zn. Transition elements of the present invention are present in the catalyst in an amount ranging from 0.1 to 50 wt % based on total weight of the catalyst or alternatively 0.1 to 30 wt % or alternatively 0.1 to 15 wt %. Transition elements may be present alone or in mixtures in the catalyst of the present invention, however whether alone or in combination, the total amount of transition metal present in the catalyst ranges from 0.1 to 50 wt % based on total weight of the catalyst.

Catalysts may include support materials, e.g. alumina, silica, silicon carbide, magnesia, zirconia, titania, and combinations thereof; as well as a carrier, such as a monolithic carrier comprising, e.g., cordierite, metal or ceramic. Supports may be modified, stabilized or pretreated to achieve structural stability under the operating conditions.

Preferably, the ethane, carbon dioxide, and the OMS catalyst are contacted at a temperature from 550° C. to 800° C., alternatively from 600° C. to 700° C. Preferably, the flow rate is from 100 to 5000 $hr^{-1}$ total gas hourly space velocity (GHSV), alternatively from 500 to 2500 $hr^{-1}$ GHSV, alternatively from 1000 to 2000 $hr^{-1}$ GHSV.

In addition to ethane and carbon dioxide, inert carrier gasses may be present, e.g., nitrogen. Inert carriers do not participate in, and are unaffected by, the reactions of concern.

Ethylene carbonylation catalysts and conditions are well known, and are described, e.g., in U.S. Pat. No. 6,284,919. Typical catalysts include, e.g., those having a Group VIII metal, e.g. palladium, and a phosphine ligand, e.g. an alkyl phosphine, cycloalkyl phosphine, aryl phosphine, pyridyl phosphine or bidentate phosphine.

In some embodiments of the invention, the products of reaction of ethane and carbon dioxide, which comprise ethylene and carbon monoxide, are contacted with an ethylene carbonylation catalyst, along with an alcohol. The ethylene and carbon monoxide stream may be passed into a different reactor for carbonylation, or alternatively, into another portion of the same reactor. The alkyl propionate product can be converted to an alkyl acrylate in an oxidative dehydrogenation process.

Unreacted ethane and carbon dioxide may be present in the product stream from reaction of ethane and carbon dioxide, as well as in the product stream from carbonylation. After separation of the carbonylation product stream, ethane and carbon oxides may be recycled to the input of the reaction of ethane and carbon dioxide. Trace amounts of ethylene and alcohol may also be present. Unreacted ethylene and alcohol from the carbonylation reaction may be recycled to the input of the carbonylation reaction.

In some embodiments of the invention, the alcohol is methanol, the alkyl propionate is methyl propionate and the alkyl methacrylate is methyl methacrylate. In these embodiments, the method represents an integrated process for producing methyl methacrylate starting from ethane and carbon dioxide.

In some embodiments of the invention, the ethylene and carbon monoxide products from the reaction of ethane and carbon dioxide are subjected to a hydroformylation reaction to produce propionaldehyde, as described, e.g., in U.S. Pat. No. 4,408,079. The propionaldehyde product can be oxidized to propionic acid or condensed with formaldehyde to produce methacrolein, which in turn can be used to produce methacrylic acid.

In some embodiments of the invention, the method further comprises polymerization of the methyl methacrylate product to provide an integrated process for producing methyl methacrylate polymers or copolymers starting from ethane and carbon dioxide.

In some embodiments of the invention, methanol is used to produce methyl methacrylate as described herein, and the methyl methacrylate then is transesterified with other alcohols to produce other alkyl methacrylates.

In some embodiments of the invention, the ethylene and carbon monoxide are copolymerized. Preferably, a palladium compound is used as a catalyst, e.g., palladium cyanide, aryl phosphine complexes of palladium or palladium halides, or tetrakis triarylphosphine platinum complex. Polymerization processes are described, e.g., in U.S. Pat. Nos. 3,530,109 and 3,694,412. The ethylene-carbon monoxide polymer can be converted to a thermosetting compound by heating.

In some embodiments of the invention, ethane, carbon dioxide and oxygen are reacted under millisecond contact times resulting in an autothermal reaction. Millisecond contact times are times less than one second, alternatively less than 900 milliseconds, alternatively less than 500 milliseconds, alternatively less than 100 milliseconds, alternatively less than 50 milliseconds, alternatively less than 10 milliseconds. In some embodiments of the invention, ethane and carbon dioxide react either in a single reactor or in staged reactors to provide improved heat balance.

EXAMPLES

Preparation of Potassium

Manganese Oxide Catalyst

OMS Catalysts were produced by the following procedure: in separate containers, 16.8 g of $MnSO_4.H_2O$ and 6 mL of concentrated $HNO_3$ were dissolved in 60 mL distilled water and 11.8 g of $KMnO_4$ was dissolved in 200 ml distilled water. $KMnO_4$ solution was then added dropwise into the $MnSO_4$ solution, resulting in a brownish colloidal suspension. The colloidal suspension was then refluxed at 100° C. for 12 h. The resulting products were filtered and washed with deionized water to remove the undesired reaction by-products. Finally, the material was dried in oven at 120° C. for 6-12 h.

Synthesized K-OMS-2 was calcined in tube furnace at 800° C. for 2 h in $N_2$ at a flow rate of 500 cc/min. The resulting material was used as the supporting material. The Fe-loaded catalyst was obtained by impregnating 1.06 g of 1M Fe$(NO_3)_3.9H_2O$ aqueous solution on 1.5 g of the supporting material, followed by shaking 30 minutes on the shaker. After drying in 120° C. for 2 h to remove the water, the obtained material was calcined under 650° C. with the rate of 5° C./min for another 2 h. The Fe content was 3 wt %.

Preparation of Comparative Iron Oxide Catalyst by Incipient Wetness (IW) Method

A commercial sample of $CaCO_3$ (20 g, ACS reagent, 99%+ purity, measured pore volume of ~0.60 $cm^3g^{-1}$) was treated with 6 mL of a homogeneous solution of Fe(III) nitrate (non-ahydrate form containing ~13 wt % Fe). The incipient wetness process was carried out at room temperature by dropwise addition of the iron nitrate solution with constant mixing (manual stirring followed by Vortex mixer for 30 min) to ensure uniformity).

After 30 min of soaking in closed containment, the resulting brown paste-like precursor was placed in a ceramic dish, and the large chunks were pulverized to 2-3 mm size grains. The mixture was then calcined in a programmable isothermally box furnace as follows: 4 hr at 80° C. then drying at 120° C. for 4 hr, followed by a calcination step carried out at 300° C. for 2 hr with continuous air-purge (5 Standard Liters Per Minute). The catalyst was then charged into the reactor for additional heat treatment prior to the catalytic evaluation step. This calcination step took place at 600° C. for one hour while a gaseous stream consisting of 10% $O_2$ and 90% $N_2$ was passing at 100 $cm^3$/min over the catalyst bed. x-ray fluorescence (XRF) analysis of the calcined catalyst gave the following results for wt % of various metals:

| Ca | Fe | Si | Na | Sr | Mg | Cr |
|---|---|---|---|---|---|---|
| 35.7 | 4.1 | 0.08 | 0.09 | 0.03 | 0.01 | 0.01 |

Testing of Catalysts

The catalysts above were tested in the following manner:

The oxydehydrogenation of ethane with $CO_2$ was carried out in a vertical, fixed bed quartz reactor. A fixed amount of catalyst (1.0 cc) was charged to the center section of the ½" quartz tube reactor. Inert quartz chips were employed above and below the catalyst to provide support, and a feed pre-heat zone. The reactor was installed in a 3-zone electrically heated tube furnace. Independent thermocouples permitted both control of the reactor temperature on the outer surface as well as the monitoring of the internal catalyst bed temperature via a center thermowell. Feed gas flows were controlled by Brooks mass flow controllers. All catalysts tested were pre-treated in-situ with a 100 cc/min flow of a 10% $O_2$ in $N_2$ blend at 600° C. for 1 hour. Following pretreatment, the catalyst was heated to the evaluation temperature in flowing $N_2$ prior to being exposed to the feed mixture. At the desired evaluation temperature, the catalyst was exposed to the 80:80:40 $C_2H_6$/$CO_2$/$N_2$ feed mixture and product analysis commenced. Catalysts were generally evaluated for several hours at 1200 $hr^{-1}$ GHSV. Product analyses were by gas chromatography. Product accountabilities were generally 98+%. Ethane and $CO_2$ conversion as well as $C_2H_4$ and CO selectivities were calculated as follows:

$$\text{Ethane conversion} = \frac{\text{Moles of ethane reacted}}{\text{Moles of ethane in the feed}} \times 100$$

$$\text{CO}_2 \text{ conversion} = \frac{\text{Moles of CO}_2 \text{ reacted}}{\text{Moles of CO}_2 \text{ in the feed}} \times 100$$

$$\text{Ethylene selectivity} = \frac{\text{Moles of ethylene in the product}}{\text{Moles of feed ethane reacted}} \times 100$$

$$\text{CO selectivity} = \frac{\text{Moles of CO in the product}}{\text{Moles of feed CO}_2 \text{ reacted}} \times 100$$

Carbon deposition on the spent catalysts was minimal and did not impact product accountabilities.

The data for the two catalysts are given in Table 1 below.

| Catalyst | KOMS-2 | Fe—CaCO$_3$ |
|---|---|---|
| Flow rate (cc/m) | 200 | 200 |
| Temperature (° C.) | 800 | 800 |

-continued

| Catalyst | KOMS-2 | Fe—CaCO$_3$ |
|---|---|---|
| C$_2$H$_6$ conversion (%) | 80.4 | 77.2 |
| CO$_2$ conversion (%) | 36.0 | 29.2 |
| C$_2$H$_4$ selectivity (%) | 93.0 | 90.4 |
| CO selectivity (%) | 100.0 | 100.0 |
| C$_2$H$_4$ yield (%) | 74.8 | 69.7 |
| CO yield (%) | 49.4 | 378.0 |
| CH$_4$ yield (%) | 6.7 | 4.8 |
| C$_2$H$_4$:CO molar ratio | 1.51 | 1.84 |

The data above indicate that the KOMS-2 catalyst has greater activity for converting ethane and CO$_2$ over the Fe—CaCO$_3$. Surprisingly, although it has greater activity, the KOMS-2 catalyst also exhibits greater ethylene selectivity, resulting in a higher ethylene yield. Typically, as oxidation catalysts have increased oxidation activity, selectivity lowers. Finally, the KOMS-2 catalyst gives a more favored ethylene:CO ratio (closer to 1:1 is preferred for ethylene carbonylation reactions).

The invention claimed is:

1. A method for producing a mixture of ethylene and carbon monoxide by contacting ethane and carbon dioxide with a mixed valent catalyst comprising synthetic cryptomelane or octahedral molecular sieve at a temperature of at least 550° C. to produce ethylene and carbon monoxide.

2. The method of claim 1 wherein the catalyst comprises a single transition element or a mixture of transition elements and further wherein the single transition element or the mixture of transition elements is present in the catalyst in a range of 0.1 to 50% by weight based upon total weight of the catalyst.

3. The method of claim 2 wherein the transition element is iron.

4. The method of claim 2, further comprising steps of:
(a) contacting an alcohol, and said ethylene and carbon monoxide with an ethylene carbonylation catalyst to produce an alkyl propionate; and
(b) separating the alkyl propionate from byproducts and starting materials.

5. The method of claim 4 further comprising reacting the alkyl propionate with formaldehyde to produce an alkyl methacrylate.

6. The method of claim 4 wherein the alcohol is methanol, the alkyl propionate is methyl propionate and the alkyl methacrylate is methyl methacrylate.

7. The method of claim 6, further comprising polymerizing the methyl methacrylate.

8. The method of claim 2, further comprising co-polymerizing the ethylene and carbon monoxide.

9. The method of claim 2, further comprising combining said ethylene and carbon monoxide with hydrogen to produce propionaldehyde.

10. The method of claim 9, further comprising condensing the propionaldehyde with formaldehyde to produce methacrolein.

* * * * *